(12) United States Patent
Figulla et al.

(10) Patent No.: US 9,125,738 B2
(45) Date of Patent: Sep. 8, 2015

(54) PROSTHETIC VALVE FOR REPLACING AN ATRIOVENTRICULAR HEART VALVE

(76) Inventors: Hans Reiner Figulla, Jena (DE); Alexander Lauten, Jena (DE)

(*) Notice: Subject to any disclaimer, the term of this patent is extended or adjusted under 35 U.S.C. 154(b) by 76 days.

(21) Appl. No.: 13/979,022

(22) PCT Filed: Dec. 22, 2011

(86) PCT No.: PCT/EP2011/006573
§ 371 (c)(1),
(2), (4) Date: Nov. 26, 2013

(87) PCT Pub. No.: WO2012/095159
PCT Pub. Date: Jul. 19, 2012

(65) Prior Publication Data
US 2014/0088696 A1    Mar. 27, 2014

(30) Foreign Application Priority Data
Jan. 11, 2011 (WO) ................ PCT/EP2011/000082

(51) Int. Cl.
*A61F 2/24*    (2006.01)
(52) U.S. Cl.
CPC .................................. *A61F 2/2412* (2013.01)
(58) Field of Classification Search
CPC .............................. A61F 2/2412; A61F 2/2418
USPC ................................................. 623/2.1–2.19
See application file for complete search history.

(56) References Cited

U.S. PATENT DOCUMENTS

| | | | |
|---|---|---|---|
| 8,652,203 B2* | 2/2014 | Quadri et al. | 623/2.11 |
| 2006/0058872 A1 | 3/2006 | Salahieh et al. | |
| 2009/0112309 A1* | 4/2009 | Jaramillo et al. | 623/1.26 |
| 2009/0276040 A1 | 11/2009 | Rowe et al. | |
| 2011/0040374 A1* | 2/2011 | Goetz et al. | 623/2.11 |
| 2012/0078353 A1* | 3/2012 | Quadri et al. | 623/2.11 |
| 2012/0303116 A1* | 11/2012 | Gorman et al. | 623/2.11 |
| 2013/0144381 A1* | 6/2013 | Quadri et al. | 623/2.11 |
| 2013/0190861 A1* | 7/2013 | Chau et al. | 623/2.18 |
| 2014/0222136 A1* | 8/2014 | Geist et al. | 623/2.11 |
| 2014/0277390 A1* | 9/2014 | Ratz et al. | 623/1.26 |
| 2014/0277427 A1* | 9/2014 | Ratz et al. | 623/2.38 |
| 2014/0350669 A1* | 11/2014 | Gillespie et al. | 623/2.18 |

FOREIGN PATENT DOCUMENTS

| | | | |
|---|---|---|---|
| WO | 2010-121076 A2 | 10/2010 | |
| WO | 2011-057087 A1 | 5/2011 | |
| WO | WO 2011057087 A1 * | 5/2011 | |

* cited by examiner

*Primary Examiner* — Suzette J Gherbi
(74) *Attorney, Agent, or Firm* — Inskeep IP Group, Inc.

(57) ABSTRACT

A prosthetic valve for replacing an atrioventricular heart valve comprises an annular body (2) on which valvular cusps are fastened and which is adapted to be inserted into a valve annulus (18) of the heart (20). The annular body has a plurality of anchor elements which are connected thereto on the ventricle side and optionally other anchor elements which are connected to the annular body on the atrium side. Said anchor elements extend radially outside the annular body and substantially parallel to its outer wall.

10 Claims, 5 Drawing Sheets

PROSTHETIC VALVE FOR REPLACING AN ATRIOVENTRICULAR HEART VALVE

RELATED APPLICATIONS

Figure 1:
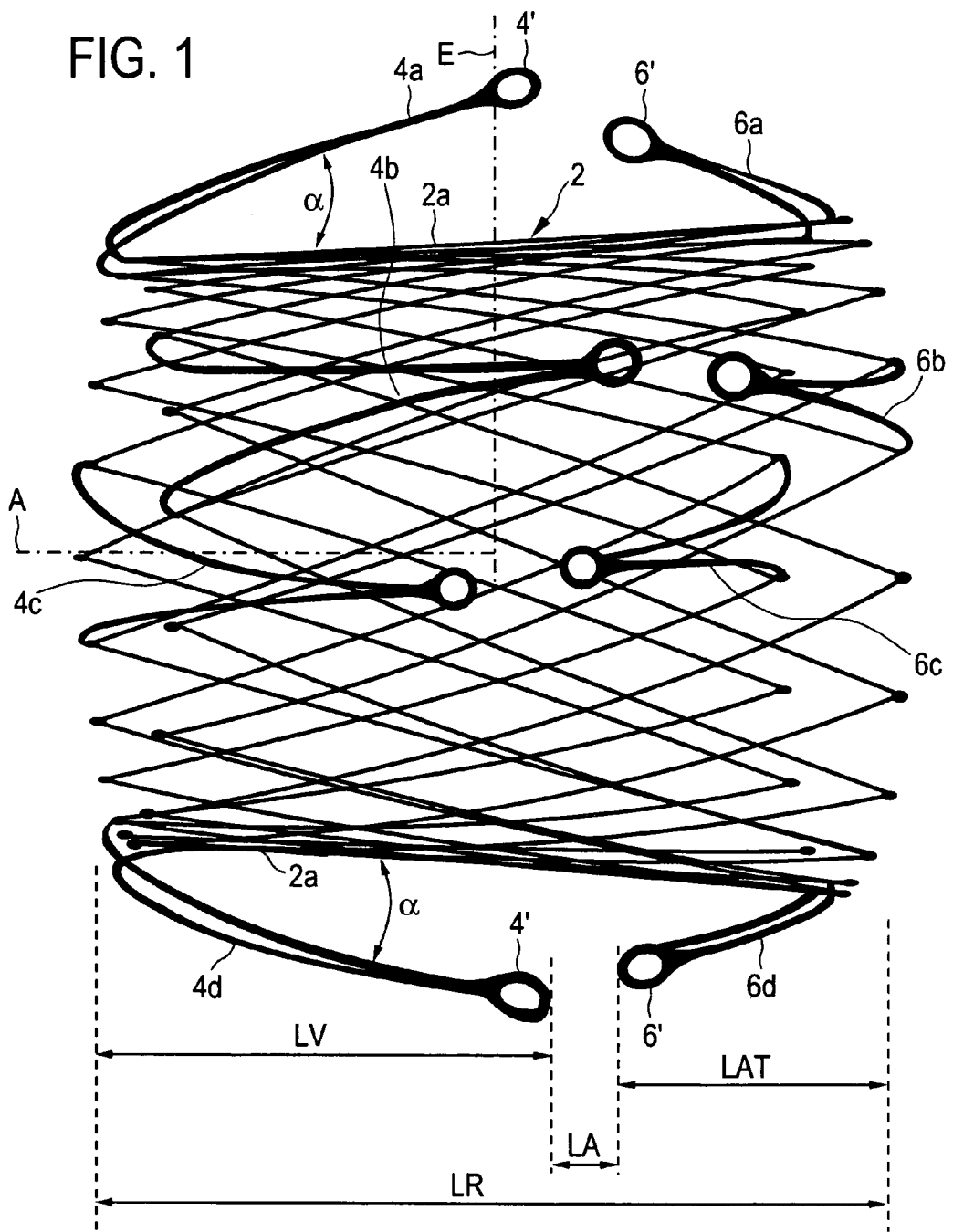

The present invention is the U.S. National Phase of and claims priority to International Patent Application No. PCT/EP2011/006573, International Filing Date Dec. 22, 2011, entitled Prosthetic Valve For Replacing An Atrioventricular Heart Valve (Klappenprothese zum Ersatz einer Artrioventrikularklappe des Herzens), which claims priority to International Patent Application No. PCT/EP2011/000082, International Filing Date Jan. 11, 2011, entitled Valve Prosthesis For Replacing An Atrioventricular Valve Of The Heart (Klappenprothese zum Ersatz einer Artrioventrikularklappe des Herzens), both of which are incorporated herein by reference in their entireties.

The invention relates to a valve prosthesis for replacing an Atrioventricular valve of the heart, i.e, the mitral valve or the tricuspid valve.

In patients with functional impairment of a heart valve, the use of open-heart surgery to insert a prosthetic valve (replacement valve) is often associated with increased risks due to the general condition of the patient. Consequently, heart valve prostheses are increasingly implanted in a minimally invasively manner via a catheter.

The prior art recognizes the use of highly compressible stents with replacement heart valve leaflets attached therein that are deliverable through a catheter for advancement to the site of the heart valve to be replaced and there releasable. For example, a balloon-expandable or self-expandable stent develops a radial expansion force in released state which force causes or at least promotes anchoring of the replacement valve prosthesis. A replacement aortic valve which can be anchored by a radial expansion force for such an anchoring of a valve prosthesis is particularly suitable at the place of a dysfunctional aortic valve. See, for example, EP 1994913 A2, EP 1469797 B1, EP 1259195 B1, WO 2007/051620 A1, WO 2007/048529 A1, EP 1980220 A1, WO 01/64137 A1, EP 1255510B3, and U.S. Pat. No. 5,411,552.

However, the mitral valve of the heart, which is the valve between the left atrium and the left ventricle, is not very suitable for a replacement prosthesis anchored mainly by a radial expansion force of a stent positively (by friction) anchored on the spot, since the annulus of the mitral valve, due to its flexibility, provides an inadequate counter-abutment for prosthesis anchorage.

One objective of the present invention is to provide a valve prosthesis that allows replacement of an atrioventricular valve, which is implantable using a catheter, and allows for stable and orthotropic positioning and anchoring.

An inventive valve prosthesis for the replacement of an atrioventricular valve of the heart is provided that has

- an annular, i.e. ring shaped, body attached to which valve leaflets, which are known as valvular cusps, are attachable and which annular body is adapted to be inserted into a valve annulus of the heart, and
- a plurality of anchor members that are connected to the ventricular side of the annular body,
- wherein
- the anchoring elements extend radially outward of the annular body and are substantially parallel to its outer wall and.

The anchoring elements above (which may be referred to as guides or arms) preferably extend along the outside of said annular body to the valve annulus of the heart so that, by means of these anchoring members, the valve prosthesis as a whole is supported, in particular against axially acting forces in the closed state of the replacement atrioventricular valve.

The axial length of said ring body in relation to the length of the above-described anchoring elements is preferably chosen such that the anchoring elements extend over at least half the axial length of the annular body.

According to a preferred embodiment of the invention, the anchoring elements are bent in the axial direction directly at the ventricular end of the annular body. Thus, the anchoring elements do not protrude substantially radially outwardly from the annular body on the ventricular side, but extend along the annular body at a small radial distance on the exterior of the annular body. The small radial distance between the anchoring elements and outer wall of the annular body is dimensioned so that the anchoring elements clamp, in particular, leaflet tissue and chordae between the anchoring elements and the outer wall of the annular body. Through this clamping action of the anchoring elements, the stable positioning of the replacement atrioventricular valve is further promoted.

To prevent undesirable rubbing of the anchoring elements against heart tissue, in particular in the region of the annulus, the free ends of the anchoring elements are rounded, for instance by transiting into a ring.

According to another embodiment of the invention, the replacement valve prosthesis additionally includes anchoring elements on the atrial side, similar to the above-described anchoring elements on the ventricular side, that are connected to the annular body and extend along the annular body and substantially parallel to the outer wall of the annular body. This extension also preferably extends up to the annulus of the heart, so that the valve prosthesis is fixed and supported virtually on all sides at the annulus by the ventricular-side anchoring elements and the atrial-side anchoring elements.

A preferred embodiment of the invention provides that said annular body has approximately a truncated cone-shape, wherein preferably the diameter of the atrial side of the truncated cone is greater than the diameter of the truncated cone on the ventricular side. Another embodiment provides that the annular body has a truncated and/or an elliptical diameter (corresponding to the elliptical circumference of atrioventricular valves).

The annular body may be formed, for example, of a wire mesh, in particular of zig-zag shaped wires, as it is generally known as such in stent technology.

In addition, the anchoring elements are preferably integrally formed with the wire mesh of the annular body. The number of anchoring elements, for example, on the ventricular side of the annular body should be at least three, but preferably four or more. The same applies, where relevant, to the number of anchoring elements on the atrial side of the annular body.

The anchoring elements are preferably arranged at regular spatial intervals so that, with the use of four anchor members, the anchor members are separated by an angle of 90°, respectively.

The annular body and the anchor members may be made from a suitable material such as a metal or metal alloy, for example as are known to those skilled in the stent technology, or a metal braiding, for example of a memory metal.

During systole, the ventricle is to be sealed off from the atrium. This sealing is provided by the valve prosthesis. A force corresponding to the full blood pressure acts on the heart valve leaflets of the prosthesis. The valve prosthesis must be stably and durably orthotropically anchored to counter this force. The invention utilizes the insight that this force substantially acts in the direction of the central axis of the annular body (corresponding with the direction of the central axis of the annulus) so that the anchoring must absorb tensile forces in this direction.

Therefore, the inventive valve prosthesis provides necessary anchoring forces without generating friction between the prosthetic valve and the annulus. Rather, the valve prosthesis, during systole in which it assumes the closed state, is anchored by supporting forces acting in the axial direction, that are introduced via the anchoring elements into the surrounding tissue, in particular on the ventricular side of the annulus. In addition, the supporting and stabilizing of the valve prosthesis can be promoted through a clamping action between the anchoring elements and mitral valve leaflets or chordae.

The size and elastic properties of the annular body are chosen so that, when placed in the heart, no significant radial expansion forces act on the valve annulus to expand the valve annulus of the heart.

Heart valve leaflets, which may be used with the valve prosthesis of the invention and can be attached to or in the annular body, can be selected from the prior art as disclosed, for example, in U.S. Pat. No. 5,411,552 and EP 1,255,510 B3. For example, a valve leaflet obtained from a pig or a biological heart valve formed from a pericardium flap may be sewn into the annular body.

The invention provides a heart valve prosthesis with a ventricular-sided anchoring, which enables stable and orthotropic anchorage and positioning of the heart valve prosthesis. The anchoring prevents movement of the valve prosthesis in the axial direction. As used herein, axial direction, radial direction, and circumferential direction, refers to the annular body of said valve prosthesis or, in the implanted state, the annulus of the replaced Mitral or Tricuspid valve.

The inventive replacement atrioventricular valve may be balloon-expandable or self-expandable.

The replacement valve may be implanted by means of a catheter, transepitally, transapically via the apex of the heart, or retrograde through the aorta.

The positioning of the valve prosthesis with a catheter is preferably made in a procedure such that the anchoring elements as described are released from a first end of the catheter and are then anchored by their anchoring elements and supported behind the mitral leaflets and/or between the chordae. Then, the valve prosthesis including the annular body is completely released, such that the annular body comes to rest with its center approximately at the annulus of the valve to be replaced.

The inventive anchoring elements are shaped to allow an unhindered flow of blood in the ventricle between them to provide access to the aorta and aortic valve.

In a further preferred embodiment of the invention, the axial length of the anchoring elements is adjustable, e.g. via a lockable telescopic arrangement, a threaded connection, or the like, so that the surgeon may adjust locally to the anatomical circumstances.

Figure 2:
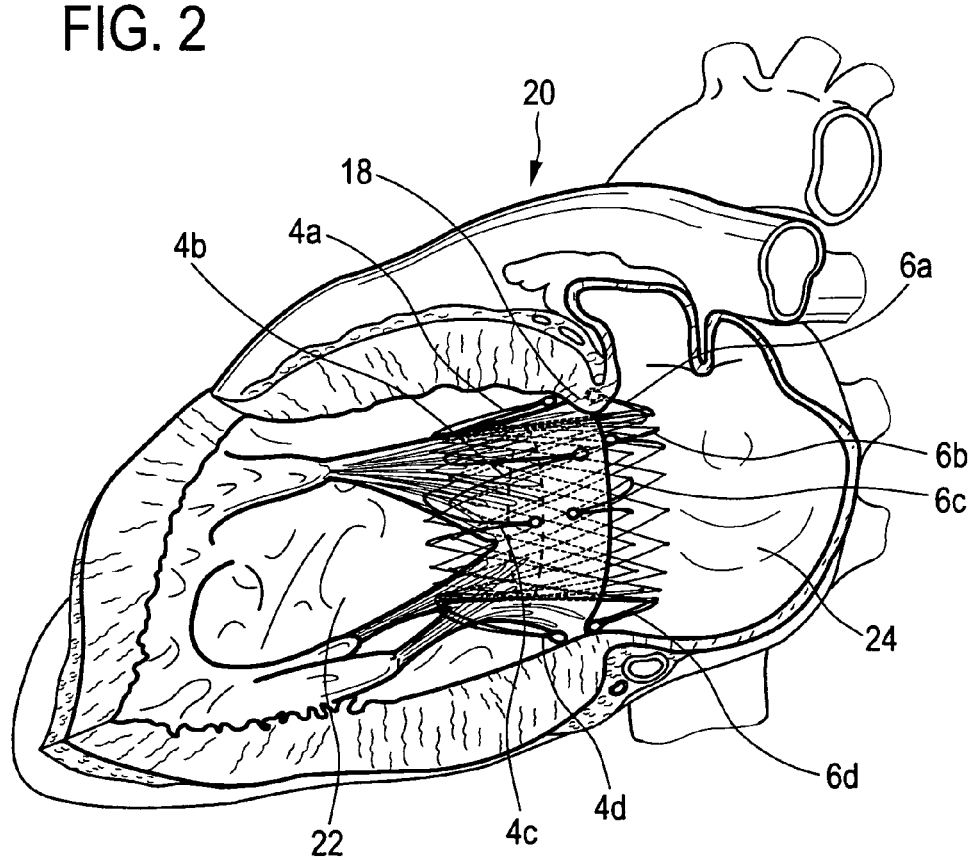
Figure 3:
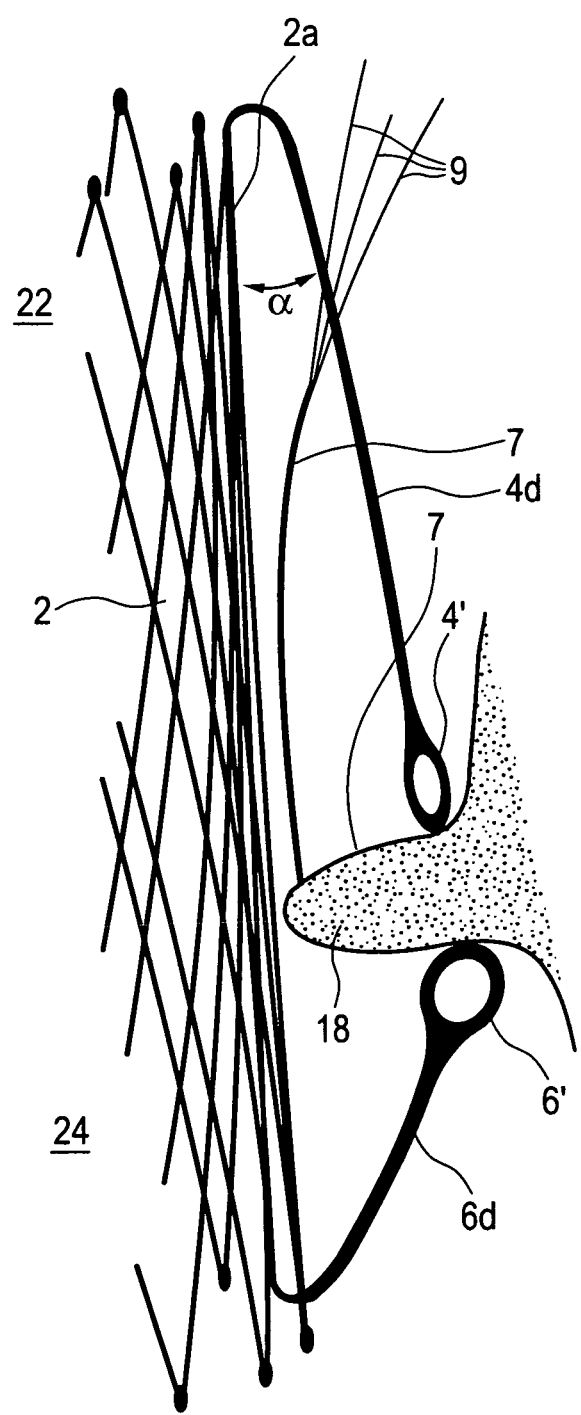
Figure 4:
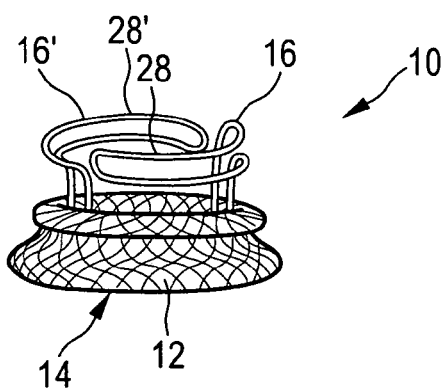
Figure 5:
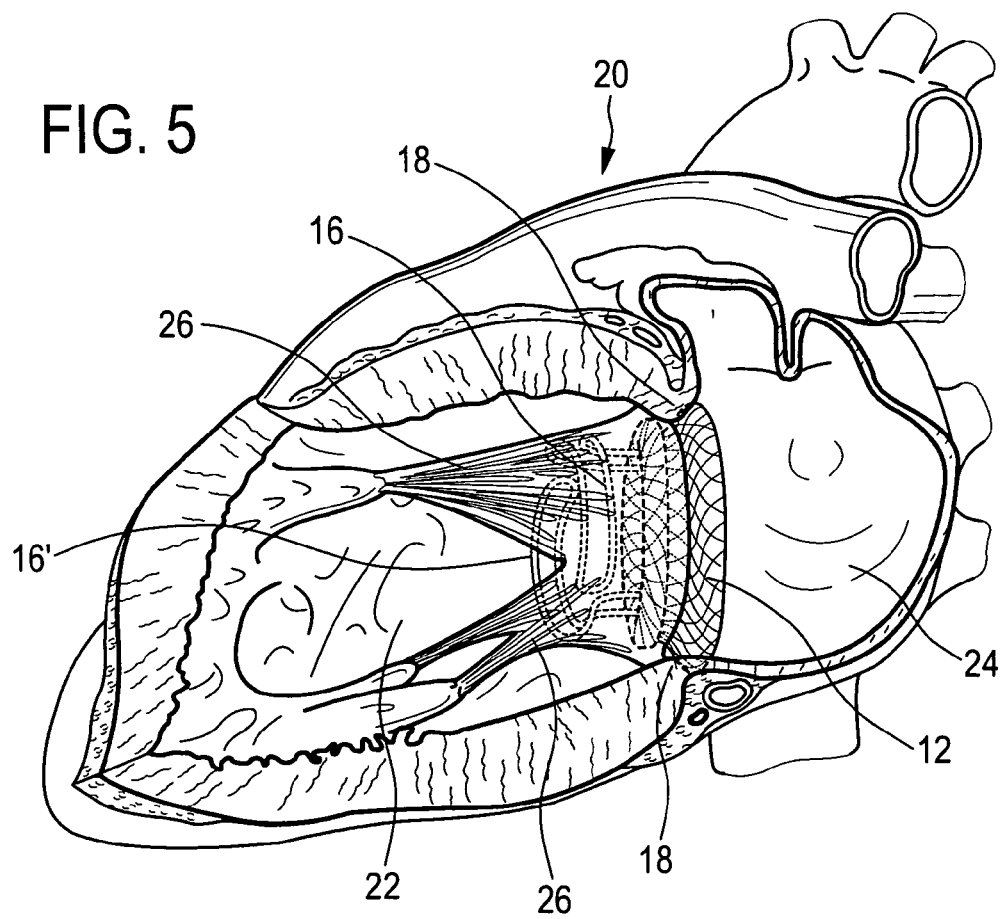
Figure 6:
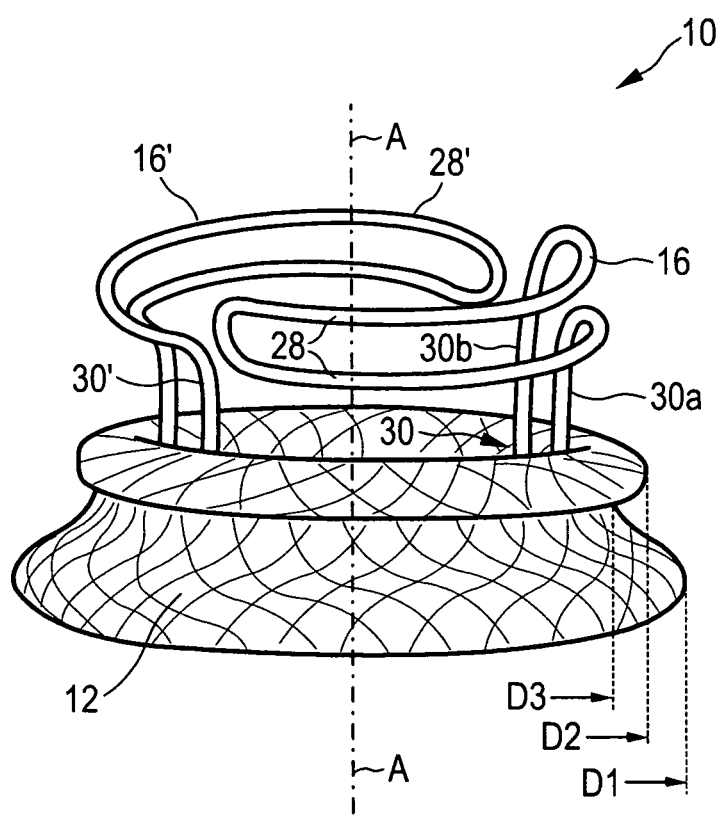

Embodiments of the invention will be elucidated with reference to the drawings, which show:

FIG. 1 a schematic valve prosthesis to replace an atrioventricular valve of the heart;

FIG. 2 the use of the prosthetic valve in a heart between atrium and ventricle;

FIG. 3 a lateral wall of the annular body of the valve prosthesis with anchoring elements and the anchoring in the area of the annulus of the heart, FIG. 4 an embodiment of a valve prosthesis for replacing an atrioventricular valve of the heart in a schematic illustration;

FIG. 5 a valve prosthesis according to FIG. 4 in the implanted state in the heart, and FIG. 6 a valve prosthesis according to FIGS. 4 and 5 on an enlarged scale.

The valve prosthesis to replace an atrioventricular valve of the heart illustrated in the FIGS. 1, 2 and 3, includes an annular body 2 into which heart valve leaflets, not shown in detail, are mounted. Known systems, for example cusps of pericardium or leaflets from porcine heart valves may be sewn into the annular body 2 and used for the replacement heart valve leaflets. The annular body 2 is formed from a wire mesh and the elastic characteristics of the wire as well as the dimensions of the annular body 2 are chosen so that the annular body, in use of the valve prosthesis as a mitral valve or tricuspid valve, in contrast to typical a stent, does not cause a substantially radially oriented force that expands the natural valve annulus.

A metal shape-memory, for example Nitinol, may be used for the wire mesh of the annular body 2.

As the figures illustrate, the annular body 2 is rotationally symmetrical about the axis A. In the embodiment shown in FIGS. 1 to 3, the annular body 2 is frustum-shaped with a somewhat larger diameter at the atrial side (right-hand side in FIG. 1) than on the ventricular side (left-hand side in FIG. 1). In a modification of the embodiment described above with a rotationally symmetrical annular body, the annular body may also have an elliptical circumference (girth).

On the ventricular side (FIG. 1, left), the wire mesh of the annular body 2 integrally transitions into four anchoring elements 4a, 4b, 4c, 4d. The anchoring elements extend, starting from the end of the annular body 2 on the ventricular side, directly radially outside the outer wall 2a of the annular body 2 in the direction of the center of the annular body 2. In this case, the arm-shaped anchoring elements 4a, 4b, 4c, 4d form an angle [alpha] α with the outer wall 2a of the ring body 2. Each anchoring element is secured with a pair of circumferentially spaced struts on the annular body to stably anchor each member in position relative to the annular body.

Over the radial center plane E of the annular body 2 in the direction of the atrium, the free projecting ends of anchoring elements 4a, 4b, 4c, 4d are rounded in order to avoid friction with tissue. In the illustrated embodiment the rounding is accomplished by the anchoring members passing into rings 4'.

Furthermore, in the exemplary embodiment according to FIGS. 1 to 3, on the side of the annular body 2, atrial anchoring elements 6a, 6b, 6c, 6d similar to the above-described ventricular-side anchoring elements are connected to the annular body 2. These anchoring elements 6a, 6b, 6c, 6d also transition towards the radial central plane of the annular body into rounded free ends, for example in the form of rings 6'.

FIG. 1 also shows the axial dimensions of the components. The axial length LV of the ventricular-side anchor members 4a, 4b, 4c is so dimensioned that the anchoring members, project beyond the radial center plane E (FIG. 1) and in the implanted state of the valve prosthesis, the rounded ends rest against the heart annulus (see FIG. 3).

The axial length LAT of the atrial side anchoring elements 6a, 6b, 6c, 6d is such that the anchoring elements rest on the atrial side of the annulus with their rounded free ends.

Thus, the axial distance between the ends 4' of the ventricular-side anchoring elements and the ends 6' of the atrial-side anchoring elements is so dimensioned that it corresponds approximately to the axial thickness LA of said annulus. The total length LR of the annular body is illustrated in FIG. 2. It is dimensioned so that ventricular-side end of the annular body extends in the region of the chordae of the heart valve, so that the anchor members 4a, 4b, 4c, 4d can be inserted through the interspaces between the chordae and so can be pushed behind the flat tissue of the papillary muscles to the annulus. From these anatomical characteristics, as shown in FIG. 2, the axial length LR results for the valve prosthesis.

FIG. 3 shows the outer wall 2a of the annular body 2 on a side facing the annulus 18 of the heart valve, mitral leaflet 7, and chordae 9.

As explained above, the anchoring elements 4d, etc. are positioned between the chordae 9 and behind the leaflets and terminate in supporting apposition at their free ends 4' with the ventricular side of the annulus 18.

The angle α between the arm-like anchoring elements and the outer wall 2a of the annular body 2 is dimensioned so that the papillary muscle tissue 7 is pinched between the anchoring elements 4a, 4b, 4c, 4d and the outer wall 2a of the annular body so that the stable positioning of the valve prosthesis is thereby promoted.

FIGS. 4 to 6 show another embodiment of a prosthetic valve.

The valve prosthesis 10 for replacement of an atrioventricular valve of the heart shown in FIG. 4 has an annular body 12 in which heart valve leaflets, not shown in detail, are fixed. Known systems for heart valve flaps 14 may be used, for example leaflets from pericardium, or obtained from porcine heart valves, which are sewn into the annular body 12. The annular body 12 is formed from a wire mesh and the elastic characteristics of the wire and the dimensions of the annular body 12 are selected so that the annular body, in use of the valve prosthesis as a mitral valve or tricuspid valve, and in contrast to a typical stent, does not produce a radial expansion force that substantially expands the natural valve annulus.

For the wire mesh of the annular body 12, a metal shape-memory can be used, for example, Nitinol.

As FIGS. 4, 5 and 6 illustrate, the annular body is rotationally symmetrical about the axis A. The atrial side diameter D1 of the annular body 12 is greater than the diameter D2 of the ventricular side and this, in turn, is greater than a central diameter D3 of the annular body 12.

As the figures illustrate, the ventricular-side anchor members 16, 16' protrude from the annular body 12 in the axial direction. As FIG. 5 illustrates, these anchor members 16, 16' protrude into the ventricle 22. The annular body 12 is positioned with its central portion, that is the portion of reduced diameter D3, in the annulus of the mitral valve 18. FIG. 5 thus illustrates the use of the valve prosthesis between the left atrium and left ventricle. The area of the annular body 12 having an enlarged diameter D1 abuts the atrial side of the annulus 18 and the fixes valve prosthesis in its open state when blood flows from the atrium 24 into the ventricle 22.

The anchoring elements 16, 16' are in the embodiment, two components respectively, namely on the one hand, first arms 30a, 30b which extend substantially parallel to the axis A of the annular body 12 and transition at their ends on the ventricular side of the annular body into loop-shaped bends that form components 28, 28' of the anchoring elements (FIG. 6).

In the illustrated embodiment, an arm 30 has two arm components 30a, 30b for the rotationally fixed connection between anchoring part 16 having annular body 12, which arm components extend substantially parallel to the axis A of the annular body and on their ends at the ventricular side transition to loop-type bend components 28, 28' of the anchoring elements that extend circumferentially. The anchor members 16, 16' are formed of a suitable metal wire.

The anchor members 16 are, according to a given anatomical situation, dimensioned such that the distance from the annulus 18 to the ventrical-facing end of the anchoring part is in the range of from 5 to 40 mm, preferably in the range of 5 to 20 mm or in the range of 10 to 25 mm.

Similar to a stent-valve prosthesis, the described valve prosthesis is highly compressible and can be positioned via a minimally invasive catheter in the heart, namely in particular transepitally, transapically via the apex of the heart, or even retrograde via the aorta. Catheter techniques known by those of skill in the art can be used for this purpose.

The procedure for insertion of the described valve prosthesis includes that the anchoring elements 16,16' first be released from the catheter at the area of the valve being replaced. The anchoring of the embodiment illustrated in FIGS. 4-6 by anchoring members 16' is accomplished by rotation of the annular member 12 with the anchorage elements 16, 16' attached thereto, which with its components 28, 28' for example hook in the chordae or also the native semilunar valve. The rotation can be accomplished by rotation of the catheter itself or by a pusher in the catheter, which allows a rotary engagement with the annular body 12. After this engagement and anchoring of the anchoring elements in the tissue, such as the chordae tendineae of the native or seminular valve then occurs, the full release of the valve prosthesis from the catheter, wherein the diabolo-shaped annular body with its central portion of reduced diameter is fixed in the annulus 18, as illustrated in FIG. 2.

In a modification of the embodiment described above, the anchoring components 28, 28' can be modified so that they do not extend in the circumferential direction, but radially outward so that they can be moved by spreading after release into anchoring engagement with the chordae or in anchoring engagement with native leaflets, according to the anatomical conditions.

The invention claimed is:

1. A valve prosthesis for replacing an atrioventricular valve of a heart, the prosthesis comprising:
    a ring-shaped body to which valvular cusps are attached and which is adapted to be inserted into a valve annulus of the heart,
    a plurality of anchoring elements connected to the ring-shaped body at its ventricular side and extending at least partially radially outside and essentially parallel to the outer wall of the ring-shaped body, and
    a plurality of anchoring elements connected to the ring-shaped body at its atrial side and extending outside and essentially parallel to the outer wall of the ring-shaped body
    an axial distance between ends of the plurality of ventricular side anchoring elements and ends of the plurality of atrial side anchoring elements is so dimensioned that it corresponds approximately to the axial thickness of said annulus to produce a clamping action between the anchoring elements and the mitral valve leaflets or chordae
    wherein the anchoring elements extend at the ventricular side of the ring-shaped body over at least half of the axial length (LR) of the ring-shaped body.

2. The valve prosthesis according to claim 1, wherein the axial length (LV) of the anchoring elements is adjustable.

3. The valve prosthesis according to claim 1, wherein the ends of the anchoring elements have a ring-shape or partial ring-shape.

4. The valve prosthesis according to claim 1, wherein the anchoring elements attached to the ring-shaped body at its atrial side extend along less than half of the axial length (LR) of the ring-shaped body.

5. The valve prosthesis according to claim 1, wherein the ends of the anchoring elements attached at the atrial side to the ring-shaped body have a ring-shape or partial ring-shape.

6. The valve prosthesis according to claim 1, wherein the ring-shaped body is frusto-conical, wherein the atrial side has a larger diameter than the ventricular side.

7. The valve prosthesis according to claim 1, wherein the ring-shaped body is made of a mesh, in particular by zig-zag-shaped wires.

8. The valve prosthesis according to claim 1 wherein the anchoring elements are attached to the ring-shaped body via two struts, respectively extending at a distance along the circumference of the ring-shaped body.

9. A valve prosthesis for replacing an atrioventricular valve of a heart, the prosthesis comprising:
    a ring-shaped body to which valvular cusps are attached and which is adapted to be inserted into a valve annulus of the heart,
    a plurality of anchoring elements connected to the ring-shaped body at its ventricular side and extending at least partially radially outside and essentially parallel to the outer wall of the ring-shaped body, and
    a plurality of anchoring elements connected to the ring-shaped body at its atrial side and extending outside and essentially parallel to the outer wall of the ring-shaped body
    an axial distance between ends of the plurality of ventricular side anchoring elements and ends of the plurality of atrial side anchoring elements is so dimensioned that it corresponds approximately to the axial thickness of said annulus to produce a clamping action between the anchoring elements and the mitral valve leaflets or chordae
    wherein the ends of the anchoring elements have a ring-shape or partial ring-shape.

10. A valve prosthesis for replacing an atrioventricular valve of a heart, the prosthesis comprising:
    a ring-shaped body to which valvular cusps are attached and which is adapted to be inserted into a valve annulus of the heart,
    a plurality of anchoring elements connected to the ring-shaped body at its ventricular side and extending at least partially radially outside and essentially parallel to the outer wall of the ring-shaped body, and
    a plurality of anchoring elements connected to the ring-shaped body at its atrial side and extending outside and essentially parallel to the outer wall of the ring-shaped body
    an axial distance between ends of the plurality of ventricular side anchoring elements and ends of the plurality of atrial side anchoring elements is so dimensioned that it corresponds approximately to the axial thickness of said annulus to produce a clamping action between the anchoring elements and the mitral valve leaflets or chordae
    wherein the ends of the anchoring elements attached at the atrial side to the ring-shaped body have a ring-shape or partial ring-shape.

* * * * *